United States Patent [19]

Youngs

[11] Patent Number: 5,004,642
[45] Date of Patent: Apr. 2, 1991

[54] SELF-ADHERENT FOAM WRAPPING MATERIAL

[76] Inventor: Janene Youngs, R.R. 4 P.O. Box 954, Harrisburg, Ill. 62946

[21] Appl. No.: 568,024

[22] Filed: Aug. 16, 1990

[51] Int. Cl.⁵ ............................................. B32B 3/26
[52] U.S. Cl. ................... 428/222; 428/304.4; 428/317.3; 428/409; 428/906
[58] Field of Search ................ 428/222, 304.4, 317.3, 428/409, 906

[56] References Cited

U.S. PATENT DOCUMENTS

| 4,484,574 | 11/1984 | De Rusha et al. | 428/906 |
| 4,564,550 | 1/1986 | Tschudin-Mahrer | 428/906 |
| 4,567,091 | 1/1986 | Spector | 428/222 |

*Primary Examiner*—William J. Van Balen
*Attorney, Agent, or Firm*—Barnes & Thornburg

[57] ABSTRACT

Wrapping material formed of a foamed plastic-like material. The wrapping is formed in elongated strips and adheres to itself and most surfaces it is applied to without requiring the use of a separate adhesive.

5 Claims, 1 Drawing Sheet

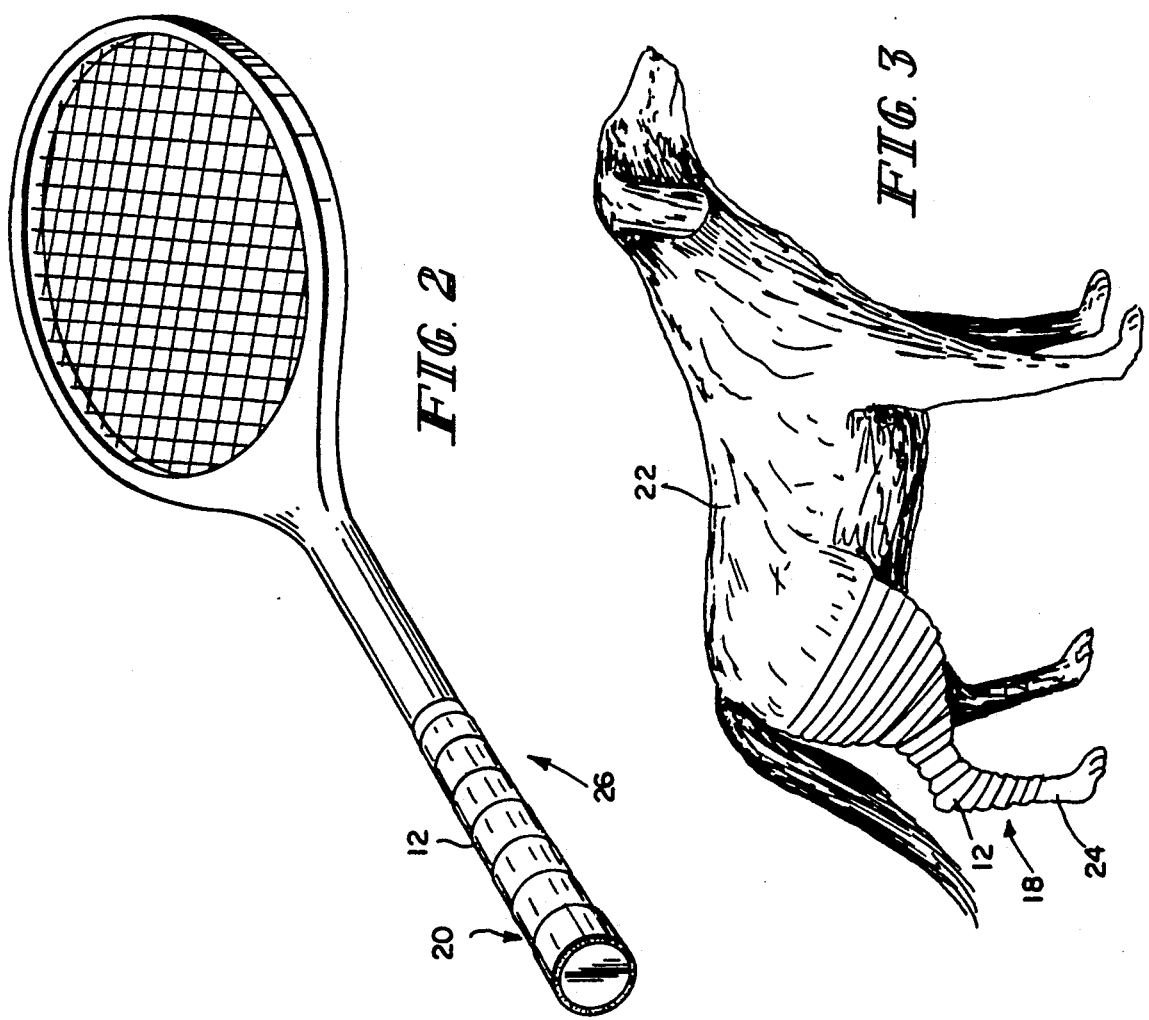

SELF-ADHERENT FOAM WRAPPING MATERIAL

SUMMARY OF THE INVENTION

This invention relates to wrappings and will have special application to a self-adherent wrap formed of elongated strips of foamed plastic.

The current state of the art in self-adherent flexible bandages and sports equipment grips is the impregnation of adhesive into a cloth membrane, which allows the bandage or grip to adhere to both itself and to the article to be wrapped. The problem with these prior bandages and grips is their limited life span and inability to be washed.

The wrapping material of this invention utilizes technology which is the base subject of U.S. Pat. No. 4,806,404, which is incorporated herein by reference. The wrapping material is formed of elongated strips of a vinyl foam which has had excess plasticizer cast into its mixture which allows the foam to adhere to itself and most surfaces. The wrap can be washed and reused since the plasticizer is incorporated directly into the final product as opposed to being added as a surface adhesive. The current preferred uses for the wrap are animal limb bandages and sport racket grips, but a number of other uses will no doubt be possible.

Accordingly, it is an object of this invention to provide for an improved self-adherent wrap.

Another object is to provide for a self-adherent wrap which is washable and reusable, while maintaining its durability.

Other objects will become apparent upon a reading of the following description.

BRIEF DESCRIPTION OF THE DRAWINGS

FIG. 1 is a perspective view of the wrap of this invention.

FIG. 2 is a perspective view of the wrap in use as a tennis racket grip.

FIG. 3 is a perspective view of the wrap in use as an animal bandage.

DESCRIPTION OF THE PREFERRED EMBODIMENT

The preferred embodiment herein described is not intended to be exhaustive or to limit the invention to the precise form disclosed. It is chosen and described to explain the principles of the invention, and its application and practical use to enable others skilled in the art to utilize its teachings.

FIG. 1 illustrates the wrapping material 10 of this invention. Wrap 10 is formed of a foamed resinous material, preferably foamable PVC resin, which has incorporated thereinto a quantity of plasticizing agent which exceeds the amount of plasticizer normally needed to soften the material. The composition and manufacturing procedure for the foam is disclosed in U.S. Pat. No. 4,806,404 which is incorporated herein by reference, and will not be described further.

Wrap 10 as shown is formed into a thin, elongated strip 12 of the foamed material and is cast onto a smooth, glossy surface release paper 14 (to improve adhesion) at between 1/64 inch in height to ¼ inch in height. The width of strip 12 is normally between ¼ inch to 6 inches depending upon intended use, and can be formed in various lengths up to at least 1000 feet. Strip 12 is normally wound on a dispensing roll 16 (not shown) with the release paper 14 separating overlapping rolls of the strip to prevent premature adhesion.

FIGS. 2-3 illustrate strip 12 in use in two fields: animal bandages 18 and sports grips 20. FIG. 3 illustrates bandage 18 wrapped about an injured leg of dog 22. To apply bandages 18 to limb 24 of dog 22, a user simply finds a starting point and unrolls the strip 12 off of its dispensing roll to wrap the strip in a spiral wound overlap fashion. Strip 12 so applied provides support for the limb 24 and also promotes healing of open wounds due to the air permeable nature of the foam. When the bandage 18 gets dirty, it may be removed, washed and reapplied quickly.

FIG. 2 illustrates the strip 12 in use as a grip 20 on a tennis racket 26. Grip 20 is unrolled and spiral wound as described above over the existing racket grip (not shown). The teachings of the foam allows strip 12 to stick fast to the old grip, and also enhances the grip of a user. Due to its inherent self-stick properties, grip 20 may be washed and reused when dirty, and resists loss of adhesion due to sweat, rain or other moisture which destroys many types of cloth grips.

Other uses will no doubt be possible for the foam. This invention is not limited to the above uses and its scope is governed only by the scope of the following claims.

I claim:

1. Wrapping material comprising an elongated strip formed of cushioned foamed material, said foamed material including a quantity of plasticizer incorporated therein in excess of the amount normally needed to soften the material wherein said strip adheres to itself and to an applied surface without use of a separate adhesive.

2. The wrapping material of claim 1 wherein said applied surface is a sporting equipment grip, said strip of sufficient tack to improve the grip of a user.

3. The wrapping material of claim 1 wherein said applied surface is an animal appendage.

4. The wrapping material of claim 1 wherein said strip is formed of washable, reusable foam, and is cast on a highly glossy release paper.

5. The wrapping material of claim 4 wherein said foam is a polyvinyl chloride foam derivative.

* * * * *